US009470655B2

(12) United States Patent
Li et al.

(10) Patent No.: US 9,470,655 B2
(45) Date of Patent: Oct. 18, 2016

(54) POLYACRYLAMIDE GELS FOR RAPID CASTING, BLOTTING, AND IMAGING, WITH STORAGE STABILITY

(71) Applicant: Bio-Rad Laboratories, Inc., Hercules, CA (US)

(72) Inventors: Lei Li, San Francisco, CA (US); Xuemei Yang, Alamo, CA (US); Christopher Belisle, Walnut Creek, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 14/850,711

(22) Filed: Sep. 10, 2015

(65) Prior Publication Data

US 2016/0003772 A1 Jan. 7, 2016

Related U.S. Application Data

(63) Continuation of application No. 14/203,351, filed on Mar. 10, 2014, now Pat. No. 9,164,058.

(60) Provisional application No. 61/793,884, filed on Mar. 15, 2013.

(51) Int. Cl.
| | |
|---|---|
| G01N 27/447 | (2006.01) |
| C08F 2/46 | (2006.01) |
| C07K 1/26 | (2006.01) |
| B65D 85/00 | (2006.01) |
| B01D 57/02 | (2006.01) |
| C08K 3/00 | (2006.01) |
| G01N 21/64 | (2006.01) |

(52) U.S. Cl.
CPC ......... *G01N 27/44747* (2013.01); *B01D 57/02* (2013.01); *B65D 85/70* (2013.01); *C07K 1/26* (2013.01); *C08F 2/46* (2013.01); *C08K 3/00* (2013.01); *G01N 21/6428* (2013.01)

(58) Field of Classification Search
CPC .................................................. G01N 27/447
See application file for complete search history.

(56) References Cited

U.S. PATENT DOCUMENTS

| | | | |
|---|---|---|---|
| 3,842,020 A | 10/1974 | Garrett | |
| 4,139,440 A | 2/1979 | Chrambach et al. | |
| 4,481,094 A | 11/1984 | Castro et al. | |
| 4,522,742 A | 6/1985 | Lee et al. | |
| 4,654,132 A | 3/1987 | Takagi et al. | |
| 5,074,981 A | 12/1991 | Fairfield | |
| 5,080,771 A | 1/1992 | Novotny et al. | |
| 5,143,646 A | 9/1992 | Nochumson et al. | |
| 5,314,595 A | 5/1994 | Fuller | |
| 5,447,612 A | 9/1995 | Bier et al. | |
| 5,464,516 A | 11/1995 | Takeda et al. | |
| 5,589,104 A | 12/1996 | Bambeck | |
| 5,753,095 A | 5/1998 | Alpenfels et al. | |
| 5,849,166 A | 12/1998 | Fuller et al. | |
| 5,993,627 A | 11/1999 | Anderson et al. | |
| 6,090,252 A | 7/2000 | Bjellqvist | |
| 6,123,219 A | 9/2000 | Cornell et al. | |
| 6,464,850 B1 | 10/2002 | Zhang et al. | |
| 6,582,574 B1 | 6/2003 | Liu et al. | |
| 6,726,821 B1* | 4/2004 | Suzuki ............. | G01N 27/44747 204/456 |
| 7,056,426 B2 | 6/2006 | Panattoni | |
| 7,569,130 B2 | 8/2009 | Edwards et al. | |
| 7,964,075 B2 | 6/2011 | Bjellqvist et al. | |
| 8,007,646 B2 | 8/2011 | Edwards et al. | |
| 8,357,416 B2 | 1/2013 | Schindler et al. | |
| 8,506,781 B2 | 8/2013 | Rowell et al. | |
| 8,945,360 B2 | 2/2015 | Petersen et al. | |
| 2003/0221963 A1 | 12/2003 | Bjellqvist et al. | |
| 2004/0137526 A1 | 7/2004 | Hanash et al. | |
| 2005/0121325 A1 | 6/2005 | Updyke et al. | |
| 2006/0118418 A1 | 6/2006 | Sivaram et al. | |
| 2006/0163067 A1 | 7/2006 | Sevigny et al. | |
| 2006/0207882 A1 | 9/2006 | Ben-Asouli et al. | |
| 2006/0237317 A1 | 10/2006 | Perez et al. | |
| 2007/0180585 A1 | 8/2007 | Rathinasabapathi et al. | |
| 2009/0049719 A1 | 2/2009 | Compton et al. | |
| 2009/0170123 A1 | 7/2009 | Donate et al. | |
| 2010/0051462 A1* | 3/2010 | Rowell .................. | B01D 57/02 204/469 |
| 2010/0089753 A1* | 4/2010 | Edwards ............ | G01N 33/6827 204/461 |
| 2011/0089035 A1 | 4/2011 | Henry et al. | |
| 2012/0234678 A1 | 9/2012 | Diller et al. | |
| 2013/0056909 A1 | 3/2013 | Panattoni et al. | |
| 2013/0306854 A1 | 11/2013 | Belisle | |
| 2014/0008226 A1 | 1/2014 | Rowell et al. | |

FOREIGN PATENT DOCUMENTS

| | | |
|---|---|---|
| EP | 0 497 448 A1 | 1/1992 |
| EP | 0 566 784 A1 | 10/1993 |
| EP | 0 808 853 A2 | 11/1997 |
| EP | 1 167 962 A1 | 1/2002 |
| JP | 4-184163 A | 7/1992 |
| JP | H05-322845 A | 12/1993 |
| JP | H07-500126 A | 1/1995 |
| JP | 10-510363 A | 10/1998 |
| JP | 2002-277438 A | 9/2002 |
| WO | 93/02115 A1 | 2/1993 |
| WO | 95/27197 A1 | 10/1995 |
| WO | 96/16724 A1 | 6/1996 |
| WO | 97/17384 A1 | 5/1997 |
| WO | 2007/076452 A1 | 7/2007 |

OTHER PUBLICATIONS

Bio-Rad Manual. A Guide to Polyacrylamide Gel Electrophoresis and Detection. 2012 (47 pages).

(Continued)

*Primary Examiner* — Jennifer Dieterle
(74) *Attorney, Agent, or Firm* — Kilpatrick Townsend and Stockton LLP

(57) ABSTRACT

Hand cast gels, and solutions for their preparation, are described.

8 Claims, No Drawings

(56) References Cited

OTHER PUBLICATIONS

Dolnik et al., "Preparation of Polyacrylamide Gell-Filled Capillaries for Capillary Electrophoresis," *J. Microcol. Sep.*, 3:155-159 (1991).

Garfin et al., "Gel Electrophoresis of Proteins," *AES Application Focus*, pp. 1-34, 2007.

International Search Report and Written Opinion from Appl. No. PCT/US2014/7022788, dated Jun. 24, 2014.

U.S. Appl. No. 12/552,104, filed Sep. 1, 2009, Granted.
U.S. Appl. No. 12/691,440, filed Jan. 21, 2010, Granted.
U.S. Appl. No. 13/371,667, filed Feb. 13, 2012, Pending.
U.S. Appl. No. 13/555,944, filed Jul. 23, 2012, Granted.
U.S. Appl. No. 13/896,572, filed May 17, 2013, Pending.
U.S. Appl. No. 13/934,936, filed Jul. 3, 2013, Pending.

Bandhakavi S, et al. "Evaluation of Stain-Free Gels for GeLC-MS Applications." Poster presented at American Society of Mass Spectrometry Annual Meeting, May 20-24, 2012, Vancouver BC, Canada.

Chang et al.; "Detection of arylsulfatase A activity after electrophoresis in polyacrylamide gels: Problems and solutions"; *Anal. Biochem.*; 97:36-42 (1979).

Edwards RA et al. "The light-induced reactions of tryptophan with halocompounds." *Photochem. & Photobiol.* 75, 362-368, 2002.

Fang Y et al. "Quantitative analysis of proteome coverage and recovery rates for upstream fractionation methods in proteomics." J. Proteome Res. 9, 1902-1912, 2010.

Ladner CL et al. "Development of indole chemistry to label tryptophan residues in protein for determination of tryptophan surface accessibility." *Protein Sci.* 16, 1204-1213, 2007.

Ladner CL et al. "Identification of trichloroethanol visualized proteins from two-dimensional polyacrylamide gels by mass spectroscopy." *Anal. Chem.* 78, 2388-2396, 2006.

Liu N, et al. "Compatibility of Criterion Stain FreeTM Gel Imaging System with Mass Spectrometric Protein Analysis." Bio-Rad Bulletin 5810. Copyright 2008.

McDonald K et al. "In-Gel Protein Quantitation Using the Criterion Stain-Free™ Gel Imaging System." Bio-Rad Bulletin 5782. Copyright 2008.

Orr et al.; "Discontinuous buffer systems for analytical and preparative electrophoresis of enzymes on polyacrylamide gel"; *Anal. Biochem.*; 45:68-85 (1972).

Piersma SR et al. "Workflow comparison for label-free, quantitative secretome proteomics for cancer biomarker discovery: method evaluation, differential analysis, and verification in serum." J. Preoteome Res. 9, 1913-1922, 2010.

Rappsilber J et al. "Stop and go extraction tips for matrix-assisted laser desorption/ionization, nanoelectrospray, and LC/MS sample pretreatment in proteomics." Analytical Chemistry 75, 663-670, 2003.

Sechi S and Chait BT. "Modification of cysteine residues by alkylation. A tool in peptide mapping and protein identification." Analytical Chemistry 70, 5150-5158, 1998.

Shevchenko A et al. "Mass spectrometric sequencing of proteins silver-stained polyacrylamide gels." Analytical Chemistry 68, 850-858, 1996.

\* cited by examiner

POLYACRYLAMIDE GELS FOR RAPID CASTING, BLOTTING, AND IMAGING, WITH STORAGE STABILITY

CROSS-REFERENCE TO RELATED PATENT APPLICATIONS

The present application is a continuation of U.S. patent application Ser. No. 14/203,351, filed Mar. 10, 2014, which claims benefit of priority to U.S. Provisional Patent Application No. 61/793,884, filed Mar. 15, 2013, which is incorporated by reference.

BACKGROUND OF THE INVENTION

Polyacrylamide gel electrophoresis (PAGE) is widely used in biotechnology laboratories for the processing of biological samples to separate the biomolecules present in the samples for identification, and in some cases to quantify the separated species. Protein mixtures, peptide mixtures, and mixtures of DNA, RNA, and fragments of DNA and RNA can all be separated on polyacrylamide gels. For protein mixtures, a particularly useful form of PAGE is SDS-PAGE where the detergent sodium dodecyl sulfate (SDS) is included in the sample. All proteins consist of linked amino acid residues and each protein folds naturally into a three-dimensional shape that is characteristic of, and distinctive for, each individual protein. Thus, both the amino acid sequence and the shape of the folded protein differ from one protein to the next. In the presence of SDS, however, proteins become denatured, i.e., they unfold and thereby lose their characteristic three-dimensional shapes. All denatured proteins therefore have the same shape and can be separated in SDS-PAGE on the sole basis of their molecular weight. Since proteins differ in the numbers and types of amino acids, different proteins generally have different molecular weights, and the range of molecular weights of common proteins is large.

Certain proteins are very close in molecular weight, however, which makes them difficult to separate in SDS-PAGE. To separate such proteins, or to optimize their resolution, SDS-PAGE is typically performed in a discontinuous gel, i.e., a composite gel that consists of a "stacking" or "stacker" gel cast above a "resolving" (also known as a "separating") gel, where the stacker gel has a lower polyacrylamide concentration and thus a higher porosity. The stacker and resolving gels meet at an interface where the stepwise change in porosity occurs, and in certain cases the interface also includes a stepwise change in pH from approximately neutral or slightly acidic (pH 6.6 to 7.0) in the stacker gel to basic (pH 8.6 to 9.0) in the resolving gel. Despite these discontinuities, solutes, buffer solutions, and electric currents can travel freely across the interface from one part of the gel to the other. The combined gels are oriented in a vertical position with the stacker gel above the resolving gel, and samples are initially placed at the top edge of the stacker gel. An appropriately polarized electrical field is then imposed to cause the proteins in the samples to migrate downward through the stacker gel toward the interface and into the resolving gel. During the initial stages of the migration, the proteins collect at the interface in a single sharp band. The proteins then continue their migration and enter the resolving gel, where the single band separates into multiple bands representing individual proteins. The percentage of acrylamide in the resolving gel can be varied to achieve optimal separation of the proteins. In general, however, large proteins will separate most readily in resolving gels of relatively low percentage while small proteins will separate most readily in resolving gels of high percentage.

Unfortunately, casting a gel is a time-consuming and labor-intensive procedure, and for this reason it has become commonplace for researchers to purchase pre-formed gels rather than to cast a gel at its point of use. Purchased gels are typically referred to as "precast gels" while those prepared in the laboratory are referred to as "hand-cast gels." Manufacturers of precast gels have developed gels that have a number of advantages over hand-cast gels. For example, the resolution in a polyacrylamide gel tends to decline after a few days of storage, and for this reason hand-cast gels are typically prepared shortly before use. Manufacturers have addressed this problem by formulating precast gels in ways that increase their longevity to a year or more. Another difficulty concerns the electric field strength at which a gel is run and the length of time involved in completing a run. Hand-cast gels are typically run at low field strength to avoid heating the gel during the run, since heating causes artifacts in the experiment, and the lower the field strength the longer the time required to achieve protein separation. Manufacturers have responded to this problem by formulating precast gels that can withstand high field strengths without showing anomalies due to heating. Disclosures of gel formulations that address these problems are found in Rowell et al., U.S. Pat. No. 8,282,800 B2 (Oct. 9, 2012), and Petersen et al., United States Pre-Grant Publication No. US 2010/0187114 A1 (Jul. 29, 2012).

Once a gel is run, the scientist typically either stains the gel in order to visualize the proteins separated within the gel or transfers the separated protein bands in the gel to a membrane for further processing or identification. Staining the gel is typically achieved by applying chemical stains or dyes which are often hazardous chemicals. Staining also takes time. Manufacturers of pre-cast gels have addressed this problem by formulating gels that enable proteins to be visualized without the use of stains or dyes, thereby eliminating the use of hazardous chemicals and reducing the amount of time required to detect the proteins. For example, Bio-Rad Laboratories (Hercules, Calif.) sells Stain-Free™ gel systems. The process of transferring proteins to a membrane is known as a "western blot," and involves performing the transfer in such a way that retains the separation of the individual proteins, and particularly the relative locations of the individual protein bands in the gel. Such a transfer allows the scientist to perform analyses that cannot be performed on a gel. Such analyses include immunoassays, for example, since the antibodies used in immunoassays are too large to enter the gel efficiently but can easily contact proteins on a membrane. All proteins, including those in stain-free gels, can be blotted to a membrane, adding further to the convenience of the scientist and the speed of the experiment. Some precast gels, like Bio-Rad Laboratories' TGX and TGX Stain-Free gels allow quicker transfer of proteins from gel to membrane.

While pre-cast gels have advantages, they also have disadvantages. One disadvantage is that they are more expensive than hand-cast gels, since the manufacturer will pass on to the user the cost of making, storing, and distributing the gels. A second disadvantage is that the user is limited to the types of gels that the manufacturers make available. With hand-cast gels, the user can customize the resolving gel by personally selecting monomer solutions of specific compositions to meet the special needs or interests of a particular experiment, but such flexibility is typically unavailable with precast gels. Despite its benefits, therefore, hand cast gels typically lack many of the desirable properties of manufactured pre-cast gels, including the ability to store gels for future use, run the gels quickly, visualize proteins without staining procedures, and quickly transfer the protein bands from the gels to membranes and confirm successful protein transfer on membrane without staining.

BRIEF SUMMARY OF THE INVENTION

Disclosed herein is a hand-cast gel system and stock solutions for use in the handcasting process, both the method and solutions offering advantages that are currently only available in pre-cast gels. These advantages include, but are not limited to, the ability to store the gel for extended periods of time (e.g. up to 30 days in bottom-open glass cassettes or even longer with sealed plastic cassettes) prior to use with little or no deterioration, the ability to run the electrophoresis experiment faster than is typically done with typical hand-cast gels, the ability to blot or transfer proteins from the gel to a membrane faster than with typical hand-cast gels, and the ability to image gels without a staining, i.e., in a "stain-free" manner. The stock solutions have the additional benefit that the solutions themselves are stable for extended lengths of time compared to some stock solutions used to make hand-cast gels.

In some embodiments, a hand cast gel system for polyacrylamide gel electrophoresis is provided. In some embodiments, the system comprises: a rigid mold that contains the polyacrylamide gel; and the polyacrylamide gel, comprising acrylamide, triethanolamine, an ampholyte selected from the group consisting of glycine and tricine, and a conjugate ampholyte consisting of an amino acid with a pKa within the range of 8.3 to 9.6.

In some embodiments, the system is capable of resolution of protein samples after the polyacrylamide gel has been stored for up to 30 days at 4 C. In some embodiments, the system is capable of electrophoresis within as short a time as 15 minutes and capable of substantially complete transfer of protein to nitrocellulose by blotting in as short a time as 3 minutes.

In some embodiments, the gel further comprises one or more of glycerol, Tris, and a halo-substituted compound that reacts with tryptophan residues upon irradiation with ultraviolet light to form a fluorescent compound. In some embodiments, the halo-substituted compound is a trichloroalkane. In some embodiments, the trichloroalkane is selected from the group consisting of chloroform, trichloroacetic acid and trichloroethanol, or mixtures thereof.

In some embodiments, the gel is discontinuous. In some embodiments, the gel is continuous.

In some embodiments, the rigid mold comprises two glass plates with the gel between the plates. In some embodiments, the rigid mold comprises a plastic cassette comprising two plates with the gel between the plates.

In some embodiments, said conjugate ampholyte is asparagine, taurine, threonine, serine, and histidine.

Also provided is a method of making the gel system as described above or elsewhere herein. In some embodiments, the method comprises: forming a mixture comprising acrylamide, a polymerization catalyst, triethanolamine, an ampholyte selected from the group consisting of glycine and tricine, and a conjugate ampholyte consisting of an amino acid with a pKa within the range of 8.3 to 9.6; adding said mixture into the mold; and incubating the mixture in the mold under conditions sufficient to generate the polyacrylamide gel.

In some embodiments, the gel is discontinuous, and the method further comprising preparing a stacking gel on the polyacrylamide gel. In some embodiments, prior to the forming, a solution comprising acrylamide/bis-acrylamide is formed and a separate solution comprising the triethanolamine, the ampholyte, and the conjugate ampholyte is formed, and combining (i) the solution comprising acrylamide/bis-acrylamide and (ii) the separate solution no more than 24 hours before the forming.

In some embodiments, (i) the solution comprising acrylamide/bis-acrylamide and (ii) the separate solution are stored separately for at least 7 days prior to the combining.

In some embodiments, the method further comprises performing electrophoresis with the polyacrylamide gel at least 7, 14, 21, or 28 days after generating the polyacrylamide gel.

Also provided is a kit for forming a polyacrylamide gel. In some embodiments, the kit comprises: a first container comprising a solution comprising acrylamide and bis-acrylamide; and a second container comprising triethanolamine, an ampholyte selected from the group consisting of glycine and tricine, and a conjugate ampholyte consisting of an amino acid with a pKa within the range of 8.3 to 9.6.

In some embodiments, the gel further comprises one or more of glycerol, Tris and a halo-substituted compound that reacts with tryptophan residues upon irradiation with ultraviolet light to form a fluorescent compound. In some embodiments, said conjugate ampholyte is asparagine, taurine, threonine, serine, and histidine. In some embodiments, the halo-substituted compound is a trichloroalkane. In some embodiments, the trichloroalkane is selected from the group consisting of chloroform, trichloroacetic acid and trichloroethanol, or mixtures thereof. In some embodiments, triethanolamine in the second container is between 10-250 mM, the ampholyte in the second container is between 50-500 mM, and the conjugate ampholyte in the second container is between 10-500 mM. In some embodiments, the gel further comprises Tris and/or glycolic acid.

Still further objects, features, and advantages will become apparent from the descriptions that follow.

DETAILED DESCRIPTION OF THE INVENTION

I. Hand Cast Gels

As noted above, handcast gels and systems comprising such gels are provided. Handcast gels as described herein can be continuous (i.e., a gel comprising only a resolving portion) or dis-continuous (i.e., a gel comprising a stacker portion and a resolving portion). In some embodiments, the gels can be stored for a considerable time before use (e.g., more than 7, 14, 21, or 28 days). In some embodiments, the gels are capable of electrophoresis within as short a time as 15 minutes (e.g., measured by the dye front running to the bottom of the gel) and in some embodiments are capable of substantially complete transfer of protein to nitrocellulose or PVDF membrane by blotting in as short a time as 3 minutes in the Bio-Rad Trans-Blot® Turbo™ Transfer System or 15 minutes in a standard tank blot apparatus. In some embodiments, the gels are capable of long storage as noted above, are capable of fast electrophoresis, and fast transfer of proteins during blotting.

Polyacrylamide gels for use in the practice of this invention are formed by the polymerization of acrylamide monomer and an acrylamide crosslinker in the presence of a polymerization catalyst according to methods well known in the art. The term "acrylamide crosslinker" denotes a molecule that reacts with acrylamide monomer or polyacrylamide chains to produce crosslinking between the chains.

Acrylamide crosslinkers known in the art can be used; a prominent and widely used acrylamide crosslinker is N,N'-methylene-bis-acrylamide, also known as "bis-acrylamide" or simply "bis." Other acrylamide crosslinkers are ethylene diacrylate (ED), diallyl tartardiamide (DATD), and dihydroxyethylene bisacrylamide (DHEBA).

The porosities of the gels can vary widely. In cases where discontinuous gels are prepared, the resolving gel generally has a lower porosity than the stacker gel. The porosities can be determined by the concentrations of the monomer and crosslinker in the monomer solutions, and, if a discontinuous gel is made, to achieve porosity discontinuity between the gels, the stacker gel monomer solution will often have a monomer/crosslinker concentration (i.e., the concentration of both monomer and crosslinker combined) that is at least about 2.0 volume percent lower than the monomer/crosslinker concentration in the resolving gel monomer solution. In certain embodiments, this concentration differential will be within the range of about 2% to about 20% by volume, and in many cases within the range of from about 4% to about 10% by volume. According to common usage in the art, the total monomer (i.e., acrylamide plus crosslinker) concentration is expressed in weight percent and referred to by the symbol T, while the proportion of crosslinker to total monomer is likewise expressed in weight percent and referred to by the symbol C. Aside from the differential between the stacker and resolving gels, the values of T and C are not critical and can vary widely. In most applications, however, T will range from about 8% to about 40%, and more often from about 10% to about 20%, in the resolving gel monomer solution, and from about 4% to about 8%, and more often from about 4% to about 6%, in the stacker gel monomer solution. The value of C can be the same in both solutions or can be greater in one than in the other. In most applications, C will range from about 2% to about 10%, preferably from about 2.5% to about 5%. Both monomer solutions will typically contain polymerization catalysts, and examples of such catalysts are ammonium persulfate (APS), N,N'-tetramethylenediamine (TEMED), riboflavin, and β-dimethylaminopropionitrile, all used in catalytic amounts that are known to those skilled in the art. A typical catalyst concentration is 0.3 to 3.0 µg per mL of monomer solution, and a common example is the combination of APS and TEMED, each at a concentration within this range. For example, 10 µL of TEMED and 100 µL of 10% (by weight) APS may be used in a monomer solution having a volume of 20 mL. If a continuous gel is prepared, the gel will generally have the properties as described for the resolving gel above.

A continuous gel can be formed by casting a gel in a vessel. A discontinuous gel can be formed by polymerizing the two monomer solutions in a common gel casting vessel, and the polymerizations can be performed in sequence or simultaneously. Thus, the monomers in the resolving gel can be allowed to polymerize in part or in full before the stacker gel monomer solution is placed above the resolving gel, but time can be saved without significant loss of sharpness of the stepwise porosity change at the interface by polymerizing both gels simultaneously. The stacker gel monomer solution can thus be placed in the vessel above the resolving gel monomer solution before substantial polymerization of the resolving gel monomer has occurred, and in fact immediately after the resolving gel monomer solution has been placed in the vessel. If one wants to polymerize both resolving and stacking gel concurrently, one generally includes glycerol or sucrose to accentuate the density difference and prevent mixing. If instead one polymerizes the resolving gel first, one can layer on water or alcohol to prevent exposure to air while the resolving gel polymerizes. After polymerization of the resolving gel, the water or alcohol is removed before the stacking gel solution is placed on top of the polymerized resolving gel.

In addition to acrylamide, the hand cast gels described herein comprise triethanolamine, an ampholyte, and an conjugate ampholyte. Among other attributes, triethanolamine increases the resistance of the gel to hydrolysis. The concentration of triethanolamine in these solutions can vary, although best results in most cases will be achieved with a concentration within the range of about 0.01 mol/L (1.5% by weight) to about 0.25 mol/L (37.3% by weight), for example about 0.05 mol/L (50 mM) to about 0.2 mol/L (200 mM), or about 0.075 mol/L (75 mM) to about 0.15 mol/L (150 mM).

The hand cast gel will also comprise one or more ampholytes and one or more conjugate ampholytes. If a discontinuous gel is prepared, the resolving gel monomer solution, and in many cases both the stacker gel monomer solution and the resolving gel monomer solution, comprise the one or more ampholytes. Exemplary ampholytes include, e.g., glycine and tricine. Suitable conjugate ampholytes are those with a $pK_a$ within the range of 8.3 to 9.6 and are typically amino acids. Examples of conjugate ampholytes are asparagine, taurine (considered an amino acid for the purposes of this application), threonine, serine, and histidine. The ampholyte may be present at a concentration within the range of, for example, about 0.05 mol/L (50 mM) to about 0.5 mol/L (500 mM), and the conjugate ampholyte may be present at a proportion relative to the ampholyte of, for example, from about 0.1 mole percent to about 65 mole percent, e.g., from about 20 mole percent to about 60 mole percent. (A mole percent representing a proportion of the conjugate ampholyte relative to the ampholyte is used herein to mean the number of moles of the conjugate ampholyte divided by the total number of moles of ampholyte and conjugate ampholyte, multiplied by 100). In most cases, the concentration of the conjugate ampholyte will be from about 100 mM to about 500 mM, and particularly from about 200 mM to about 350 mM.

Optionally, the hand cast gel can also comprise one or more halo-substituted compound that reacts with tryptophan residues upon irradiation with ultraviolet light to form a fluorescent compound. Inclusion of the halo-substituted compound allows for rapid detection of protein in the gel without a subsequent staining step. If the gel is a discontinuous gel, at least the resolving gel can contain the halo-substituted compound. Examples of halo-substituted compounds are disclosed by Edwards et al. in U.S. Pat. No. 7,569,103 B2 (Aug. 4, 2009) and U.S. Pat. No. 8,007,646 B2 (Aug. 30, 2011). These references cite the UV light-induced reaction between the indole moiety of tryptophan and various halo-substituted organic compounds, with specific mention of chloroform, trichloroethanol, and trichloroacetic acid, to produce a fluorescent compound with emissions at wavelengths in the visible range. Further disclosures are found in the following United States provisional patent applications which are co-owned with the present application: Provisional Patent Application No. 61/639,692, "Stain-Free Total Protein quantification of Complex Samples From Diverse Sources," Paulus et al., inventors, filed Apr. 27, 2012, and Provisional Patent Application No. 61/639,686, "Stain-Free Technology for Western Blot Total Normalization," Short et al., inventors, filed Apr. 27, 2012. Once the separation within the gel is complete, the gel is exposed to UV light, and the resulting emissions for individual protein bands are detected and quantified.

Any halo-substituted organic compound can be used that will enter into a chemical reaction with tryptophan to form a product that fluoresces upon exposure to excitation light. Halo-substituted organic compounds of particular interest are trihalo compounds, for example trichloro compounds and those with molecular weights of 200 or less. Trihaloaliphatic alcohols, trihaloaliphatic acids, trihaloaliphatic amines, and trihaloalkanes are all useful. Specific examples are chloroform, trichloroacetic acid, and trichloroethanol. Halo-substituted organic compounds can be used individually or in combinations.

The concentration of the halo-substituted compound in the monomer solution can vary widely and can readily be optimized in terms of the intensity of the signal that is ultimately produced. Effective and efficient results can generally be obtained with about 0.2% to about 2.0% of the halo-substituted compound in the gel, and in some embodiments from about 0.1% to about 0.5%, by volume.

In certain embodiments, a weak acid or combination of two or more weak acids is included in the gel solution (one or both monomer solutions in the case of discontinuous gels). Exemplary weak acids include citric acid, glycolic acid, maleic acid, phosphoric acid, acetic acid, and boric acid. When such an acid is included, its concentration will in some embodiments be within the range of about 0.01 mol/L (10 mM) to about 0.50 mol/L (500 mM), e.g., from about 0.03 mol/L (30 mM) to about 0.10 mol/L (100 mM). A further optional additive is a neutral salt for further band resolution. Examples of suitable salts are sodium chloride, sodium sulfate, sodium phosphate, potassium chloride, and potassium phosphate. When present, the concentration of the neutral salt will be in some embodiments within the range of about 0.01 mol/L (10 mM) to about 0.50 mol/L (500 mM), e.g., from about 0.03 mol/L (30 mM) to about 0.10 mol/L (100 mM). As in typical polyacrylamide gel preparations, the pH of the monomer solution can be adjusted to the desired range with a suitable acid, examples of which are hydrochloric acid, sulfuric acid, acetic acid, boric acid, and phosphoric acid. As needed, the pH can be adjusted to a value within the range of 6.4 to 9.0. A pH range of 6.4 to 7.0 is preferred in some cases.

In some embodiments, the gel solutions further comprise one or both of the buffers tris(hydroxymethyl)-aminomethane ("Tris") and bis(2-hydroxyethyl)amino-tris(hydroxymethyl)methane ("Bis-Tris"). In other embodiments, such ingredients are absent.

Depending on the other constituents used in the formulation, the concentration of Tris or Bis-Tris can vary, and in some embodiments is about 0.05 mM to about 200 mM.

In certain embodiments involving discontinuous gels, a viscosity-increasing additive is included in the resolving gel monomer solution to improve the ease of layering the stacker gel monomer solution above the resolving gel monomer solution, and to thereby allow the two solutions to be placed in a gel casting vessel with minimal (if any) mixing of the solutions. The vessel can thus be partially filled with the resolving gel monomer solution as a first step, followed by placing the stacker gel monomer solution in the vessel above the resolving gel monomer solution. Examples of such additives are glycerol and various sugars, an example of which is sucrose. The additive can be present in both monomer solutions, but its benefit can be achieved by including it in the resolving gel monomer solution only, and in many cases, this will be the most efficient use of the additive. Regardless of whether the additive is present only in the resolving gel monomer solution or is included both monomer solutions, the amount of the additive in either solution can vary widely and its benefits in improving the ease of layering the solutions without mixing them can be obtained over a wide concentration range. In most cases, however, best results will be obtained with glycerol or sucrose at a concentration of from about 5% to about 20% by weight in the solution(s) in which it is used, or perhaps more often, from about 5% to about 15% by weight.

As noted above, in some embodiments, a hand cast gel system is provided. For example, the system can comprise a gel as described herein within a vessel. The gel casting vessel can have any conventional shape and dimensions known for use as electrophoresis gels. The vessel can for example be a tube for a one-dimensional separation of a single sample, or a slab gel container or cassette (for example comprising two plastic, glass, or other material, plates with the gel residing between), optionally for electrophoresis of multiple samples in parallel lanes. Descriptions of slab gel cassettes are widely found in the patent literature, for example at Van Atta, D. L., U.S. Pat. No. 6,093,301 (Jul. 25, 2000); Perez, E., et al., U.S. Pat. No. 6,162,342 (Dec. 19, 2000); Fernwood, G., et al., U.S. Pat. No. 6,451,193 (Sep. 17, 2002); and Latham, M., U.S. Pat. No. 7,588,673 (Sep. 15, 2009). See also, David Garfin, Electrophoretic Methods, Academic Press, Inc. (1995).

II. Kits

Kits for handcasting the gels (continuous or discontinuous) described herein are also provided. In some embodiments, the kit comprises at least two containers containing different components of the gel, which when combined, and following addition of the polymerization agent (if not present in at least one of the solutions in the containers), result in the desired gel. Accordingly, all concentrations of the components listed below are intended to refer to stock solution concentrations. The stock solutions will be diluted/combined with acrylamide monomer to reach the final and working concentrations.

In cases involving a single monomer stock solution, the solution may contain acrylamide monomer to be used in conjunction with a triethanolamine-ampholyte-conjugate ampholyte buffer solution. In some embodiments, the solution contains 10%, 15%, 20%, 25%, 30%, 35%, 40%, e.g., from about 10-40% or 25-35% monomer at a monomer:crosslinker ratio of 37.5:1, for example. In some embodiments, the second stock solution (to be diluted/combined with acrylamide monomer to reach the final and working concentrations) comprises triethanolamine at a concentration between 10-250 mM (e.g., about 10, 25, 50, 75, 100, 150, 200, 250 mM), the ampholyte (e.g., glycine or tricine) at a concentration between 50-500 mM (e.g., about 50, 100, 150, 200, 250, 300, 500 mM), and the conjugate ampholyte (e.g., asparagine, taurine, threonine, serine, or histidine) in the second container at a concentration between 10-500 mM (e.g., about 10, 50, 100, 150, 200, 250, 300, 350, 400, 450, 500 mM). In some embodiments, the second stock solution further comprises one or more of Tris or Tris-HCl (within the range of 0.05 mM to 200 mM, for example) and glycolic acid (within the range of 10 mM to 500 mM, for example) at a pH within the range of 6.0 to 7.0, for example. The second stock solution can further comprise a halo-substituted compound (e.g., chloroform, trichloroacetic acid, or trichloroethanol, for example), for example within the range of 0.2% to 2%.

To form a gel solution, the monomer solution can be combined with the triethanolamine-ampholyte-conjugate ampholyte buffer solution, and water, in appropriate proportions to achieve the desired percent gel. For example, for discontinuous gels, a relatively high for the resolving gel solution and a lower percent gel for the stacker solution. The stacker gel solution can for example be a 4% monomer solution, and the resolving gel can for example be a 7.5%, 10%, 12%, 18%, or 20% monomer solution.

In addition, in cases where discontinuous gels are desired, stock solutions for use in preparing the two-part gels can include separate aqueous monomer solutions (i.e., each solution containing both monomer and crosslinker) for each of the two gel sections, differing in the total amount of monomer and crosslinker, with at least the resolving gel monomer solution containing some or all of the additional components described above. Alternatively, a single monomer stock solution can be used by combining the stock solution with buffer solutions at different ratios for the two gel sections. When separate monomer solutions are used for the two gels, the resolving gel solution can for example contain glycerol. A separate gel conditioning solution, to be combined with the resolving gel monomer solution at the time of preparation of the gel, can be one that contains triethanolamine and conjugate ampholyte (e.g., taurine) in addition to any of the other components listed above. The concentrations of all components in these stock solutions can be the same as the concentrations and concentration ranges set forth above. The polymerization catalyst or catalysts can be kept separate until the gels are to be cast. When the user is ready to hand cast the gels, the resolving gel monomer solution and a portion of the gel conditioning solution can be mixed together to form a first mixture, and the stacker gel monomer solution and a second portion of the gel conditioning solution can be mixed together to form a second mixture. The catalyst(s) can be added to both the first and second mixtures. The final mixtures thus prepared can be placed in a gel casting vessel, with the first mixture (for the resolving gel) added first.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A kit for forming a polyacrylamide gel, the kit comprising:
    a first container comprising a solution comprising acrylamide and bis-acrylamide; and
    a second container comprising triethanolamine, an ampholyte selected from the group consisting of glycine and tricine, and a conjugate ampholyte consisting of an amino acid with a pKa within the range of 8.3 to 9.6.

2. The kit of claim 1, wherein the gel further comprises one or more of glycerol, Tris and a halo-substituted compound that reacts with tryptophan residues upon irradiation with ultraviolet light to form a fluorescent compound.

3. The kit of claim 1, wherein said conjugate ampholyte is asparagine, taurine, threonine, serine, and histidine.

4. The kit of claim 2, wherein the halo-substituted compound is a trichloroalkane.

5. The kit of claim 4, wherein the trichloroalkane is selected from the group consisting of chloroform, trichloroacetic acid and trichloroethanol, or mixtures thereof.

6. The kit of claim 1, wherein triethanolamine in the second container is between 10-250 mM, the ampholyte in the second container is between 50-500 mM, and the conjugate ampholyte in the second container is between 10-500 mM.

7. The kit of claim 1, further comprising Tris and/or glycolic acid.

8. The kit of claim 1, wherein the kit has been stored for at least seven days.

* * * * *